United States Patent [19]

De Kalb et al.

[11] 3,936,633

[45] Feb. 3, 1976

[54] METHOD OF DETERMINING LANTHANIDIES IN A TRANSITION ELEMENT HOST

[75] Inventors: Edward L. De Kalb; Velmer A. Fassel, both of Ames, Iowa

[73] Assignee: The United States of America as represented by the United States Energy Research & Development Administration, Washington, D.C.

[22] Filed: Jan. 16, 1975

[21] Appl. No.: 541,476

Related U.S. Application Data

[62] Division of Ser. No. 321,064, Jan. 4, 1973, Pat. No. 893,939.

[52] U.S. Cl............................ 250/273; 252/301.2 R
[51] Int. Cl.²......................................... G01N 23/20
[58] Field of Search.................... 250/272, 273, 302; 252/301.2 R

[56] References Cited

UNITED STATES PATENTS

3,859,525   1/1975   Ashe et al............................ 250/273

*Primary Examiner*—Davis L. Willis
*Attorney, Agent, or Firm*—John A. Horan; Arthur A. Churm; Hugh W. Glenn

[57] ABSTRACT

A phosphor composition contains a lanthanide activator element within a host matrix having a transition element as a major component. The host matrix is composed of certain rare earth phosphates or vanadates such as $YPO_4$ with a portion of the rare earth replaced with one or more of the transition elements. On X-ray or other electromagnetic excitation, trace lanthanide impurities or additives within the phosphor are spectrometrically determined from their characteristic luminescence.

5 Claims, 7 Drawing Figures

METHOD OF DETERMINING LANTHANIDIES IN A TRANSITION ELEMENT HOST

CONTRACTUAL ORIGIN OF THE INVENTION

The invention described herein was made in the course of, or under, a contract with the UNITED STATES ATOMIC ENERGY COMMISSION. This is a division, of application Ser. No. 321,064, filed Jan. 4, 1973 now U.S. Pat. No. 3,893,939.

BACKGROUND OF THE INVENTION

Lanthanides and other rare earth elements including yttrium are often added either as a mixture, that is mischmetal, or individually to improve the properties of various steel alloys. Metallurgists have found that rare earths in parts per million quantities improve both the mechanical and plastic properties by acting as strong desulfurizing and deoxidizing agents. Present quality control methods for quantitatively determining the levels of rare earth additives within steel products involve long and laborious separation and concentration steps. Prior attempts to employ X-ray luminescent techniques have been unsuccessful due to the quenching effect imparted by iron and other transition metals.

It is particularly desirable to determine the amount of lanthanides present in alloys that are to be used in nuclear reactors and other applications involving neutron radiation. Various lanthanides, for instance isotopes of neodymium, samarium, europium, gadolinium and dysprosium, have very large cross sections for thermal neutron capture and are therefore objectionable additives to construction materials in facilities where neutron economy is important.

Lanthanide impurities or additives have been included in a large number of hosts other than the transition elements to produce phosphors that have fluorescent characteristics. These phosphors along with sample spectra are presented in "X-Ray Excited Optical Fluorescence Spectrometry. Scope of Application to Trace Rare Earth Determinations" by DeKalb, D'Silva and Fassel, Analytical Chemistry, pp. 1246-1251, Vol. 42, No. 11, Sept. 1970. Effective crystalline hosts are suggested with a wide variety of cations forming simple, binary and ternary oxides. However, none of the host materials presented in the article include transition elements from groups VIIB or VIII, particularly manganese, iron, cobalt and nickel. Moreover, copper from group IB was found to be a noneffective host material in one particular mixture. For purposes of this application, the elements of each group are defined by the periodic table given in Daniels and Alberty, Physical Chemistry, p. 473, 2d. Ed., John Wiley and Sons, Inc., New York, London, 1955, 1961.

SUMMARY OF THE INVENTION

In view of the limitations of the prior art, it is therefore an object of the present invention to provide a phosphor composition including one or more transition elements as major host components in which trace amounts of lanthanides can be made to luminesce with characteristic spectra.

It is also an object to provide a phosphor composition including one or more of the group of elements consisting of iron, nickel, cobalt, manganese and copper.

It is a further object of this invention to provide a method for the determination of lanthanide additives in transition element alloys that does not require the chemical separation of these additives from the host materials.

It is yet another object to provide a radiation interrogation technique for the determination of trace lanthanides in steel products.

In accordance with the present invention, a phosphor composition is prepared containing, as matrix host, the phosphates or the vanadates of weak fluorescing rare earth elements, particularly yttrium, scandium, lanthanum, gadolinium or lutetium and of one or more of the transition elements. The phosphor is activated by the inclusion of trace quantities of various lanthanides. On exposure to X-rays or other electromagnetic radiation, the resulting luminescence is spectrometrically analyzed to quantitatively determine the trace lanthanides.

DETAILED DESCRIPTION OF THE INVENTION

In preparing the phosphors of the present invention, acid solutions of the various elements are combined, followed by evaporation, dehydration and heating at appropriate temperatures. It is preferred that the heating temperature be maintained below that of the melting point of the lowest-melting component and that a sintering condition not be reached to obtain strong luminescent spectra. The heated oxide can be subsequently ground to a fine powder and pressed to form an integral compact to facilitate handling.

The phosphor composition will be in single or multiple phase and have the general formula $E_x M_y (AO_4)_z$. The anion within the host matrix is represented as $AO_4$ and may be either the phosphate or vanadate ion. E represents a rare earth element such as yttrium, scandium, lanthanum, gadolinium or lutetium, that will not act to quench the accumulations of excitation energy within the phosphor. The transition elements are represented by M and normally replace some of the yttrium or other rare earth within its crystal structure. Generally, none of the values of $x$, $y$ or $z$ will exceed one of the other values by a ratio of more than 10:1. It will be seen that iron, cobalt, nickel, manganese, chromium and copper are effective host materials within a luminescent phosphor. It can also be expected that other elements within groups VIIB, VIII and IB of the periodic table cited above will effectively act as phosphor host materials in conjunction with the rare earth phosphates or vanadates mentioned.

Typical phosphor host materials have been prepared with the following stoichiometric compositions: $Y_2Mn_3(PO_4)_4$, $YCr(PO_4)_2$, $Y_{0.8}Fe_{0.2}PO_4$, $Y_2Co_3(PO_4)_4$, $Y_2Ni_3(PO_4)_4$, $NaYCu(PO_4)_2$ and $Y_3Cu(PO_4)_5$. The particular stoichiometric composition for the yttrium-iron phosphate given above has been found to be the optimum for producing the most intense lanthanide luminescence for those components.

It has also been found that the lanthanide luminescence can be enhanced by the introduction of a nucleating agent to promote the crystal formation. In the case of the iron-containing phosphor, a particularly suitable agent is sodium pyrophosphate ($Na_4P_2O_7$). This agent is preferably added in sufficient amount to provide a mole to mole ratio with iron in the stoichiometric composition $Y_{0.8}Fe_{0.2}PO_4$.

The luminescence in the phosphor host matrix is provided by trace amounts of lanthanides. The more effective fluorescing lanthanide elements include Ce, Pr, Nd, Pm, Sm, Eu, Tb, Dy, Ho, Er, Tm, and Yb. In addition, gadolinium will produce ultraviolet spectral lines in many host matrices; however, its luminescence is quenched in iron. It will also be seen that manganese produces spectral emissions when this element is included in the phosphor.

In employing the method of the present invention to detect and determine lanthanides in copper, iron and various transition elements, a sample of the metal is dissolved in an acid solution and the desired phosphor prepared as described. The phosphor is exposed to an X-ray, gamma-ray, or other electromagnetic radiation source to excite any lanthanide additives or impurities that are contained. The resulting luminescence is resolved into spectral lines and compared with spectra of known compositions to determine the lanthanides contained within the sample. When manganese is present, it too can be determined by this method.

Suitable X-ray sources and spectrometers as well as detailed techniques for their use are well known in the art and are illustrated in the above-cited article and in "Analytical Applications of X-Ray Excited Optical Fluorescence Spectra: The Internal Standard Principle" by DeKalb, Fassel, Taniguchi and Saranathan, Analytical Chemistry, Vol. 40, pp. 2082–2084, Dec. 1968. For example, the phosphor is placed in a shielded chamber provided with a shuttered port for exposure to an X-ray source. A quartz lens is appropriately positioned in the chamber for focusing the sample luminescence onto the entrance slit of a grating spectrometer. The X-ray source can be a commercially-available, tungsten-target X-ray tube designed to operate at an electrical potential of 50 KV. The spectrometer can be of 25 cm focal length with a plane, diffraction grating and a fused-silica-window photomultiplier (e.g. RCA 7268). The entrance and exit slits of the spectrometer are set at 100 microns and the spectrum may be scanned at the rate of about 200 angstroms per minute as the phosphor is irradiated. The resulting photocurrent is amplified and recorded on a suitable strip chart recorder.

The method of correlating experimental and calibration data in terms of an internal standard is applicable in the instant case. A known but small amount of a lanthanide such as erbium is added along with the $Y_2O_3$ or other rare earth oxide. The concentrations of other lanthanides in the sample are correlated in a graph or other means to the optical intensity ratio of the lanthanide fluorescence to erbium fluorescence at characteristic peaks of each element. By treating data in this manner, many effects which would ordinarily influence luminescence, such as time and temperature of heating, residual impurities and X-ray power drift, are satisfactorily diminished.

The following examples are offered to illustrate the phosphor composition of the present invention, its preparation and the method of its use in determining lanthanides in transition elements.

STAINLESS STEEL

EXAMPLE I

Two 34-milligram samples of 303 stainless steel (C — 0.15% max., Mn — 2% max., Si — 1% max., Cr — 17%–19%, Ni — 8%–10%, S — 0.15% min., Fe — balance) were electrolytically dissolved in separate solutions of 10% $HClO_4$ in $CH_3COOH$. To each solution was added 158 mg of $Y_2O_3$ dissolved in 10% $HNO_3$ in $H_2O$. Then a dilute nitric acid solution containing Ce, Nd, $Sm_2O_3$, $Eu_2O_3$, $Gd_2O_3$, $Tb_2O_3$, $Dy_2O_3$ in a sufficient amount to equal 100 ppm of each lanthanide in the stainless steel was added to one of the solutions. For purposes of this application ppm refers to parts per million by weight. Both mixtures were evaporated to dryness and dehydrated at about 200°C. To each dry mixture was added 370 mg of $(NH_4)_2HPO_4$ and sufficient $NaP_2O_7$ to be in a one to one mole ratio with iron. After thorough blending, the mixtures were maintained at 850°C. for one hour. The resulting phosphors were then exposed to an X-ray source consisting of a Machlett OEG-50 X-ray tube with a tungsten target operated at a maximum input of 45 milliamperes at a potential of 50 kilovolts. The luminescent spectra were recorded during the irradiation.

Figure 1:
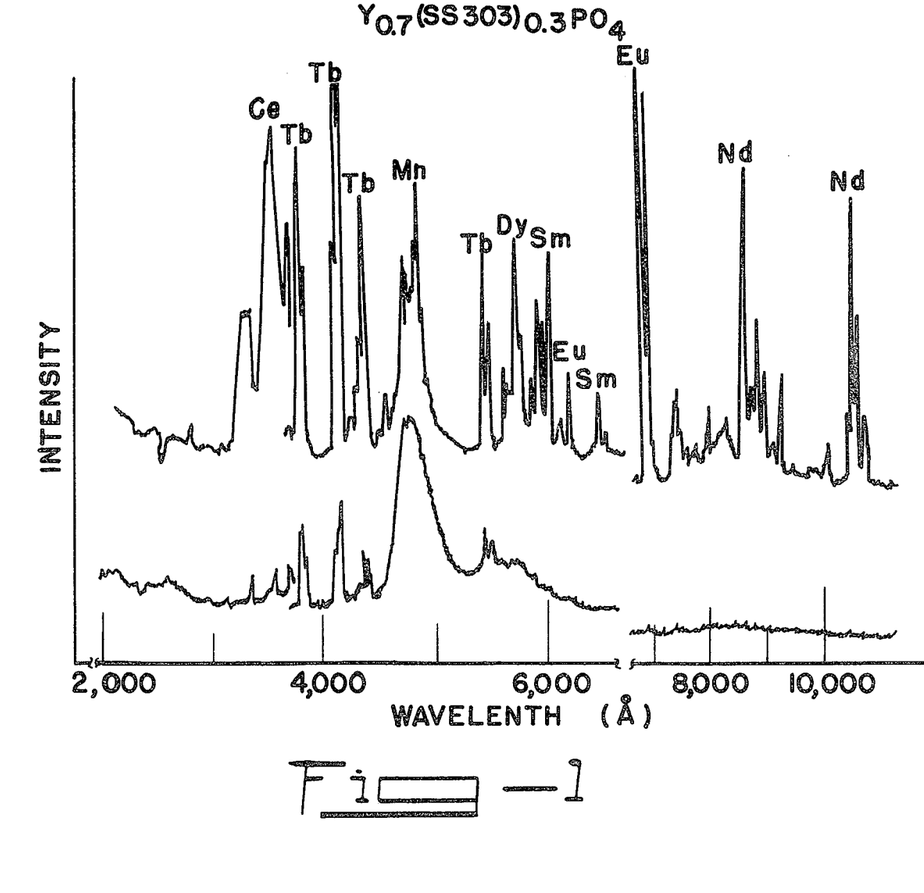
FIG. 1 shows X-ray excited luminescent spectra for phosphors containing 303 Stainless Steel with various lanthanide additives.

FIG. 1 illustrates the spectra obtained from these samples with the upper curve representing the sample including the lanthanides and the lower curve representing the dissolved stainless steel without lanthanide additives. Strong spectra lines appeared for manganese and for all of the lanthanides except gadolinium included in the doped sample. The lanthanide peaks in the lower curve are attributed to residuals within the $Y_2O_3$. These residual lanthanides can thereby be determined to correct the analysis of the other sample.

MISCHMETAL IN IRON

EXAMPLE II

Figure 2:
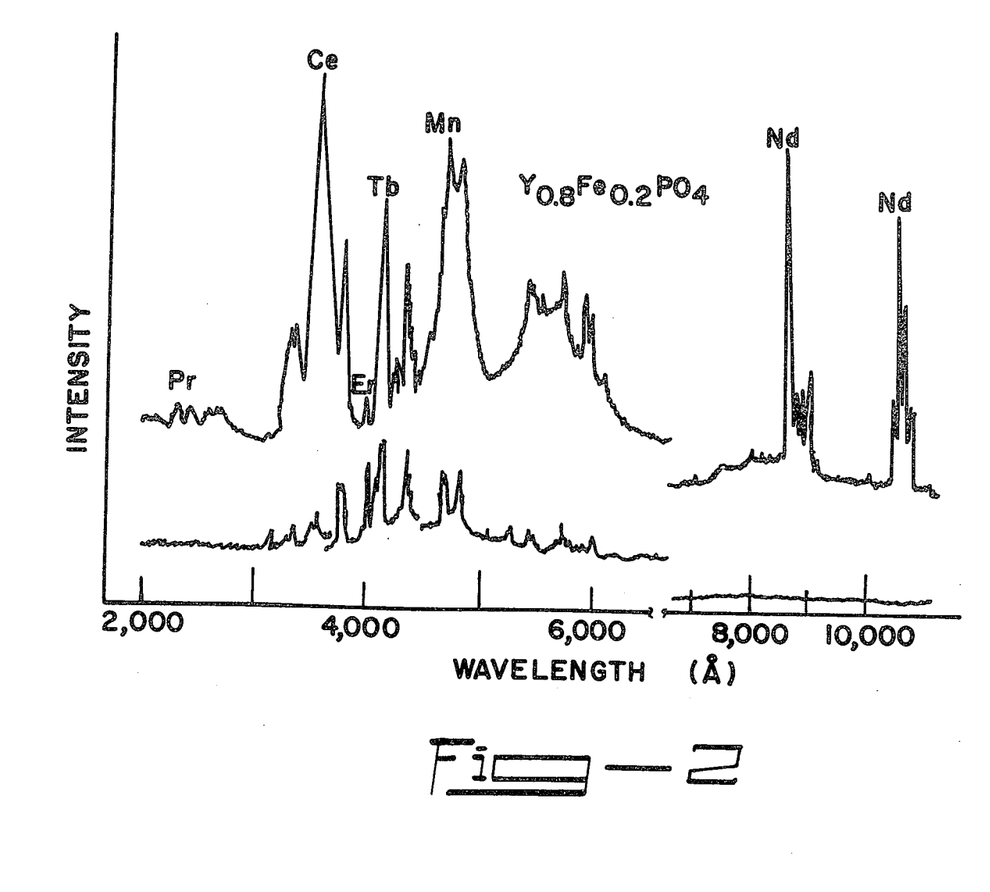
FIG. 2 shows X-ray excited spectra of phosphors containing iron.

A sample of low alloy steel containing a small amount of mischmetal and a second sample of relatively pure iron powder were dissolved and treated with $Y_2O_3$, $(NH_4)_2HPO_4$ and $Na_4P_2O_7$ in substantially the same manner as described in Example I. Sufficient $Y_2O_3$ and $(NH_4)_2HPO_4$ were added to provide a stoichiometric composition of $Y_{0.8}Fe_{0.2}PO_4$ which was previously found to be in optimum proportion for producing lanthanide luminescence. The resulting X-ray luminescent spectra of the two samples are shown in FIG. 2 with the lower curve taken from the pure iron sample and the upper curve taken from the sample of steel alloy including lanthanides. Again the peaks corresponding to terbium and other lanthanides in the lower curve are attributed to impurities in the yttrium. By comparing the spectra with that of known samples, it was found that the steel contained 500 ppm of Nd, 140 ppm of Pr and 50 ppm of Ce.

Figure 3:
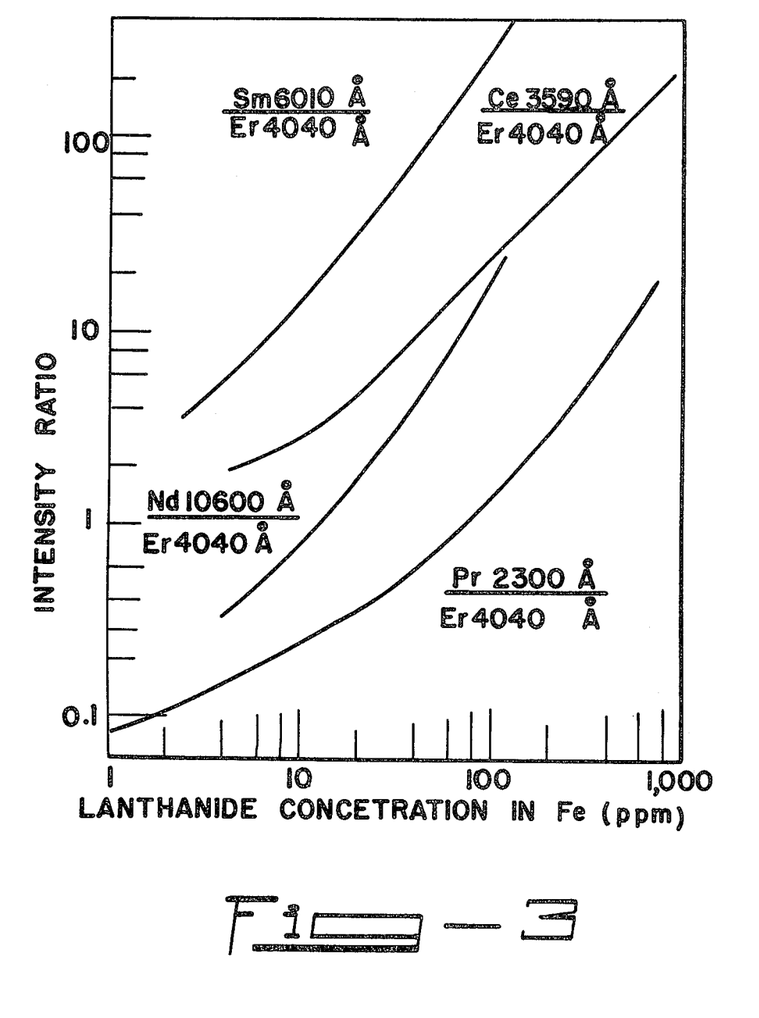
FIG. 3 is a graph of spectra line intensity ratios versus lanthanide concentration.

In the above and other iron samples, a known amount, about 20 ppm of erbium, was added along with the $Y_2O_3$ in order to introduce an internal standard into the sample. Optical intensity ratios of other lanthanides to erbium are plotted against concentration at the indicated wavelengths as illustrated in FIG. 3. As mentioned above, the use of an internal standard will satisfactorily compensate for many experimental effects. Trace quantities of Ce, Pr, Nd and Sm as low as 5 ppm have been determined by this technique.

COBALT

EXAMPLE III

Figure 4:
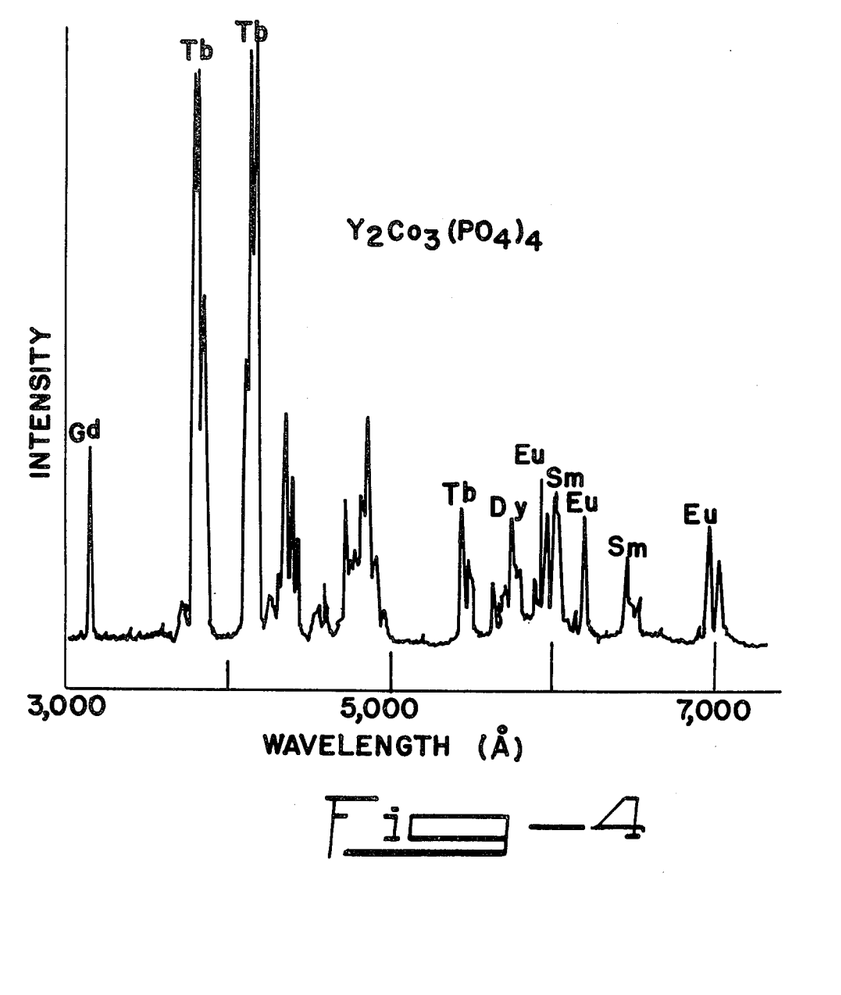
FIG. 4 is an X-ray excited spectrum for a phosphor containing cobalt.

A sample was prepared containing 100 ppm of the lanthanides Sm, Eu, Gd, Tb, and Dy in a $Y_2Co_3(PO_4)_4$ host. 0.87 gm of $Co(NO_3)_2$ 6 $H_2O$ were intermixed with 0.23 gm of $Y_2O_3$ and 0.53 gm of $(NH_4)_2HPO_4$. Approximately 0.73 ml of 0.1 nanogram/ml solution of each lanthanide were added to the dry mixture which was then dehydrated and thoroughly blended. The residue was next heated at 950°, 1050°, and 1200°C. with X-ray luminescent spectra curves produced after heating at each temperature. The strongest lines were found after the heating at 1050°C. and are shown in FIG. 4.

Figure 5:
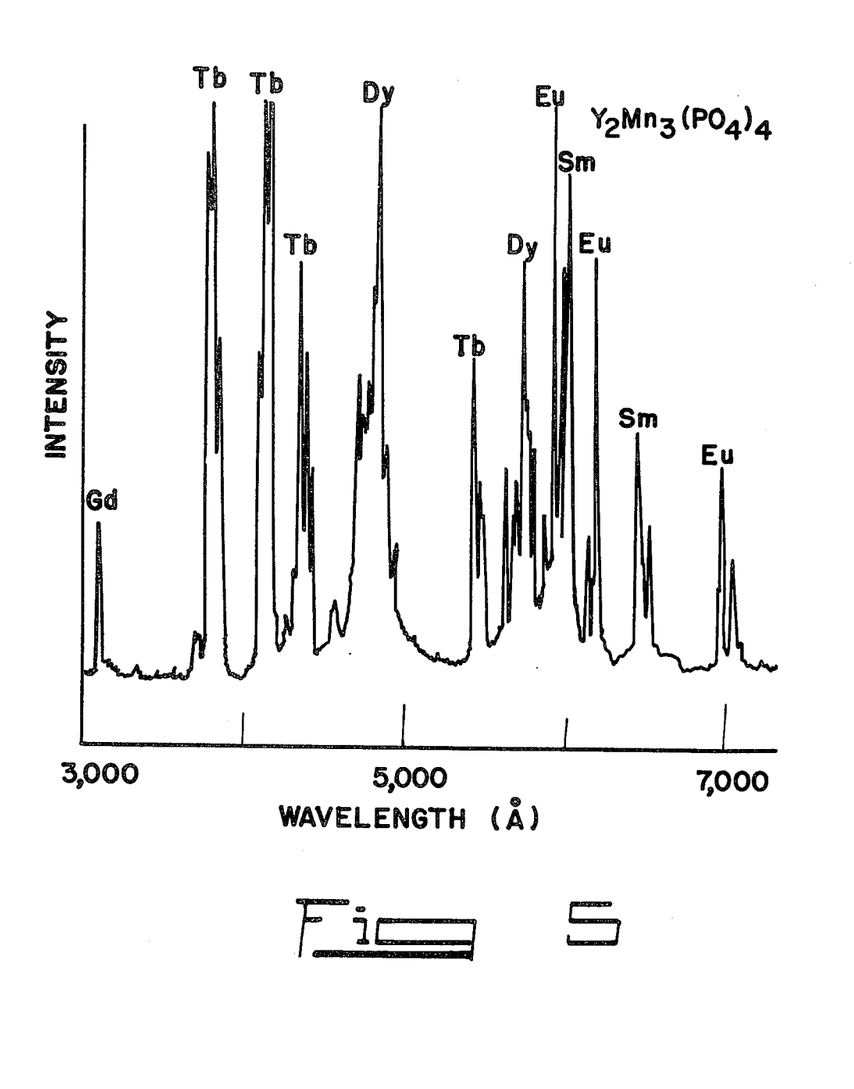
FIG. 5 is an X-ray excited spectrum for a manganese-containing phosphor.
Figure 6:
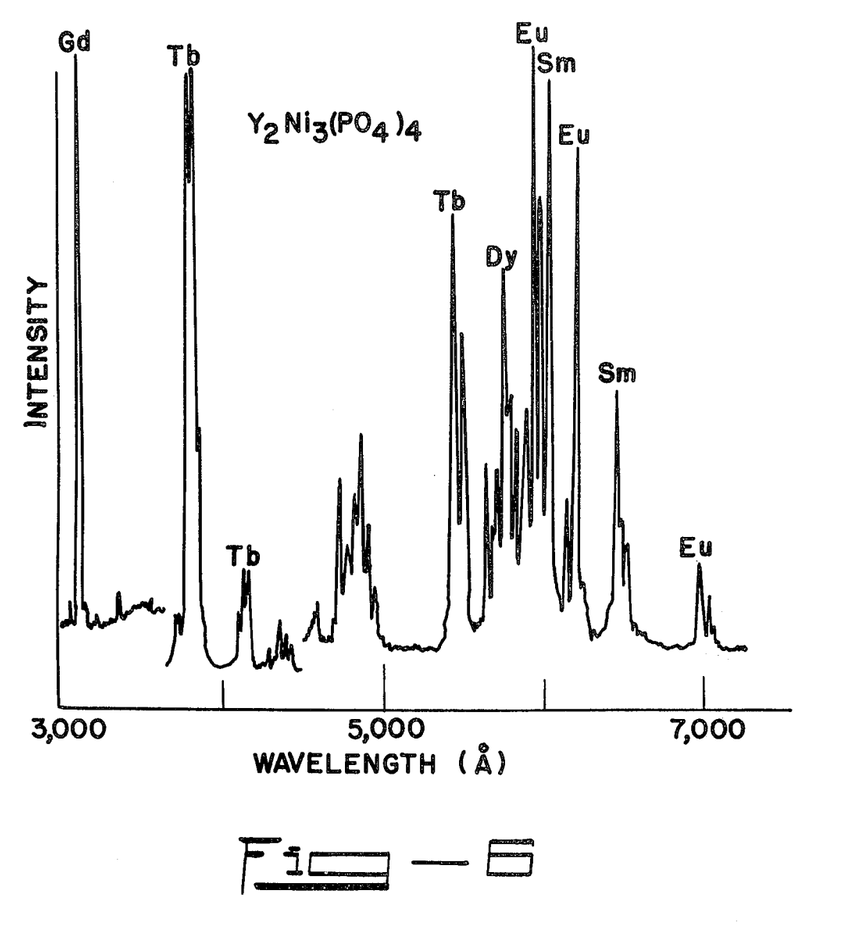
FIG. 6 is a similar spectrum for a phosphor containing nickel.
Figure 7:
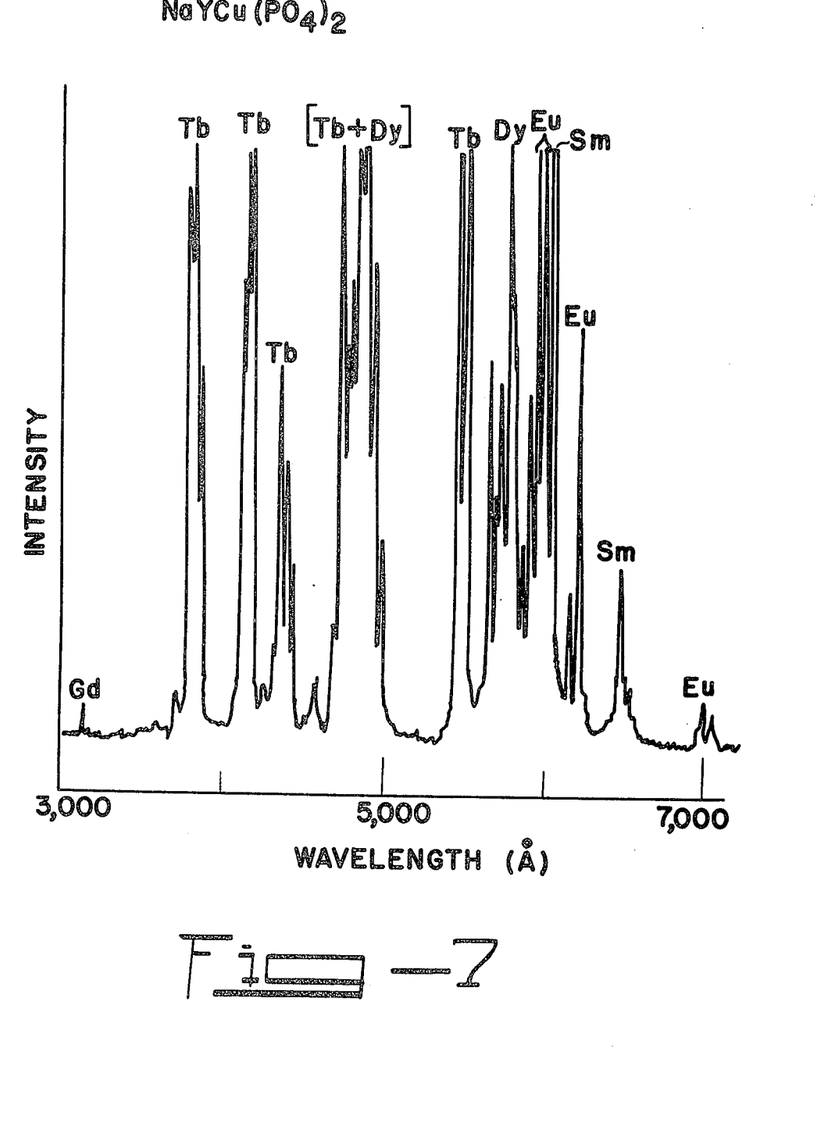
FIG. 7 is a similar spectrum for a phosphor containing copper.

Various other matrix hosts including those of stoichiometric compositions $Y_2Mn_3(PO_4)_4$, $Y_2Ni_3(PO_4)_4$ and $NaYCu(PO_4)_2$ were prepared in essentially the same manner as disclosed in the above examples. Although not essential, it was found that the addition of sodium cations within the host containing copper enhanced spectral emissions. Sm, Eu, Gd, Tb and Dy were added into each of these host materials in sufficient quantities to be equal to about 100 ppm of each named lanthanide in each phosphor. The X-ray excited luminescent spectra for these materials are illustrated in FIGS. 5, 6 and 7.

It can be seen that a new phosphor composition is presented which is useful in the detection and determination of lanthanides in steels and various transition metals. The determination method has been demonstrated at levels of 5 ppm lanthanide impurities or additives. This sensitivity is sufficient for most quality control procedures in the production of steel products. However, in nuclear reactor construction only steel products having lower concentrations of lanthanides are generally thought to be acceptable for good neutron economy. Therefore, the method at the demonstrated sensitivity may be used in this respect to identify those construction materials which clearly have too high a lanthanide content for nuclear reactor use.

The embodiments of the invention in which an enclusive property or privilege is claimed are defined as follows:

1. A method of detecting trace quantities of fluorescing lanthanides in a transition element alloy comprising:
   A. preparing a host composition including yttrium and a transition element;
   B. exciting the fluorescing elements within said composition with electromagnetic radiation;
   C. spectrometrically analyzing the resulting fluorescent radiation to quantitatively determine trace quantities of lanthanides.

2. The method of claim 1 wherein said host composition is prepared by forming a mixture of a transition metal compound, $Y_2O_3$, and $(NH_4)_2HPO_4$; and heating said mixture to a temperature below the melting point of the lowest-melting component.

3. The method of claim 2 wherein a nucleating agent consisting of $Na_4P_2O_7$ is added to said mixture of transition metal compound, $Y_2O_3$, and $(NH_4)_2HPO_4$.

4. The method of claim 1 wherein said host composition is prepared with a known quantity of a known fluorescing lanthanide to provide fluorescent radiation on X-ray excitation for spectrometrical comparison with fluorescent radiation from said fluorescing lanthanides to be quantitatively determined.

5. The method of claim 1 wherein said transition element alloy is an iron alloy and said host composition is prepared by electrolytically dissolving said iron alloy in acid solution, adding yttrium into said solution, evaporating said solution to dryness to form a dehydrated mixture and heating said mixture to a temperature below that required to effect a sintering condition.

* * * * *